United States Patent [19]

Rizvi et al.

[11] Patent Number: 5,154,843
[45] Date of Patent: Oct. 13, 1992

[54] HYDROXYALKANE PHOSPHONIC ACIDS AND DERIVATIVES THEREOF AND LUBRICANTS CONTAINING THE SAME

[75] Inventors: Syed Q. A. Rizvi, Painesville; Stephen A. Di Biase, Euclid, both of Ohio

[73] Assignee: The Lubrizol Corporation, Wickliffe, Ohio

[21] Appl. No.: 308,179

[22] Filed: Feb. 8, 1989

[51] Int. Cl.$^5$ ............... C10M 137/12; C10M 141/10
[52] U.S. Cl. ............................ 252/32.5; 252/32.7 R; 562/11; 562/13; 562/21; 562/23
[58] Field of Search ............ 252/32.5, 51.5 R, 32.7 R; 562/11, 13, 21, 23

[56] References Cited

U.S. PATENT DOCUMENTS

| | | | |
|---|---|---|---|
| 3,325,567 | 6/1967 | LeSuer | 260/928 |
| 3,403,102 | 9/1968 | LeSuer | 252/49.8 |
| 3,502,667 | 3/1970 | LeSuer | 260/268 |
| 3,513,093 | 5/1970 | LeSuer | 252/32.5 |
| 3,553,131 | 1/1971 | Hepplewhite et al. | 252/46.7 |
| 3,793,199 | 2/1974 | Schlicht | 252/32.5 |
| 3,870,750 | 3/1975 | Wollmann et al. | 562/13 |
| 4,054,598 | 10/1977 | Blum et al. | 562/13 |
| 4,206,156 | 6/1980 | Kamiya et al. | 562/11 |
| 4,215,002 | 7/1980 | Fein | 252/32.5 |
| 4,260,499 | 4/1981 | Fein et al. | 252/32.5 |
| 4,304,734 | 12/1981 | Jary et al. | 562/13 |
| 4,312,922 | 1/1982 | Caule | 428/446 |
| 4,327,039 | 4/1982 | Blum et al. | 562/13 |
| 4,514,311 | 4/1985 | Sung | 252/32.5 |
| 4,536,348 | 8/1985 | Blum | 252/51.5 R |
| 4,624,947 | 11/1986 | Blum et al. | 562/13 |
| 4,846,985 | 7/1989 | Rizvi et al. | 252/51.5 R |
| 4,876,248 | 10/1989 | Breliere et al. | 562/13 |
| 4,927,814 | 5/1990 | Gall et al. | 562/13 |

FOREIGN PATENT DOCUMENTS 2142651 5/1984 United Kingdom .

Primary Examiner—Prince Willis, Jr.
Assistant Examiner—Jerry D. Johnson
Attorney, Agent, or Firm—James L. Cordek; Frederick D. Hunter; Joseph P. Fischer

[57] ABSTRACT

This invention relates to lubricating compositions containing hydroxyalkane phosphonic acids and derivatives thereof. More specifically, this invention relates to hydroxylakane phosphonic acids which can be reacted to form salts with basic materials, including overbased detergents, dispersants and amines. These materials can be particularly useful in lubricating compositions.

The hydroxyalkane phosphonic acid is represented by the following formula:

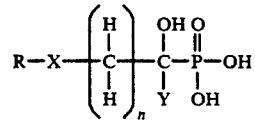

wherein X is oxygen, sulfur or a secondary amino group, n is an integer from 1 to 8, Y is hydrogen or a phosphonic acid group and R is an alkyl group having from 1 to about 100 carbon atoms.

45 Claims, No Drawings

HYDROXYALKANE PHOSPHONIC ACIDS AND DERIVATIVES THEREOF AND LUBRICANTS CONTAINING THE SAME

FIELD OF THE INVENTION

This application relates to compositions containing hydroxyalkane phosphonic acids and derivatives thereof. More specifically, this invention relates to hydroxyalkane phosphonic acids which can be reacted with basic materials, including overbased detergents, dispersants and amines to form salts. These materials can be particularly useful in lubricating compositions for improving anti-wear and extreme pressure properties of lubricating formulations, such as greases, diesel engine lubes, gasoline engine lubes, automatic transmission fluids, hydraulic fluids and various gear lubricant formulations.

BACKGROUND OF THE INVENTION

U.S. Pat. No. 3,502,667, issued to Le Suer, relates to nitrogen and phosphorus-containing succinic acid derivatives.

U.S. Pat. No. 3,403,102, issued to Le Suer, relates to lubricating compositions containing the reaction product of a polyhydric alcohol with both a high molecular weight succinic acid reactant and a phosphorus reactant.

U.S. Pat. No. 3,325,567, issued to Le Suer, relates to a process for reacting a phosphorus acid-producing compound and a succinic acid-producing compound with a polyhydroxy compound.

U.S. Pat. No. 3,513,093, issued to Le Suer, relates to a lubricating composition containing the reaction product of an alkylene polyamine with a substituted succinic acid-producing compound and a phosphorus acid-producing compound.

U.K. Pat. No. Application 2,142,651 relates to metalworking compositions containing the reaction of a polyether polyol dispersant with a phosphorus acid compound.

U.S. Pat. No. 4,514,311, issued to Sung, relates to a wear-resistant aircraft engine oil containing the reaction product of didodecyl phosphate with a poly primary amine.

U.S. Pat. No. 3,793,199, issued to Schlicht, relates to an ammonium salt of an alkyl alkane phosphonate in a lubricating composition.

U.S. Pat. No. 4,260,499, issued to Fein, relates to an alkyl phosphonate amine adduct in water-based lubricants.

U.S. Pat. No. 4,215,002, issued to Fein, relates to an alkyl phosphonate amine adduct in water-based lubricants.

U.S. Pat. No. 3,553,131, issued to Hepplewhite, relates to a lubricant containing a mixture of organo phosphonate with an organic amine.

U.S. Pat. No. 4,312,922, issued to Caule, relates to a phosphonic acid used in coating copper alloy sheets or foil.

SUMMARY OF THE INVENTION

The invention relates to compositions having hydroxyalkane phosphonic acids containing one or more heteroatoms in the alkane portion of the molecule. The hydroxyalkane phosphonic acid is represented by the following formula:

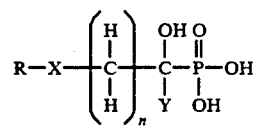

wherein X is oxygen, sulfur or a secondary amino group, n is an integer from 1 to 8, Y is a hydrogen or a phosphonic acid group and R is an alkyl group having from 1 to about 100 atoms.

An object of the invention is to provide new and useful hydroxyalkane phosphonic acids.

Another object of the invention is to provide useful salts of the hydroxyalkane phosphonic acid derivatives.

An advantage of the invention is to provide lubricating compositions with improved anti-wear and extreme pressure properties which contain salts of the hydroxyalkane phosphonic acid.

A feature of the present invention is to provide hydroxyalkane phosphonic acids that contain heteroatoms in the alkyl portion of the phosphonic acid.

Another feature of the present invention is to use mixtures of bases to form salts which provide new and useful properties in lubricating compositions.

These and other objects, advantages and features of the present invention will become apparent to those persons skilled in the art upon reading the details of the structure, synthesis and usage as more fully set forth below. Reference is made to the accompanying general structural formulae forming a part hereof wherein like symbols refer to like molecular moieties throughout.

DETAILED DESCRIPTION OF THE INVENTION

Before the present hydroxyalkane phosphonic acids, their salts and the process for making such are described, it is to be understood that this invention is not limited to a particular acid or a process described as such compounds and methods may, of course, vary. It is also to be understood that the terminology used herein is for the purpose of describing particular embodiments only, and is not intended to be limiting since the scope of the present invention will be limited only by the appended claims.

It must be noted that, as used in this specification and the appended claims, the singular forms "a", "an" and "the" include plural referents unless the context clearly dictates otherwise. Thus, for example, reference to "hydroxyalkane phosphonic acid" includes mixtures of acids, reference to "phosphonic acid salt" includes reference to mixtures of such salts, reference to "a base" includes mixtures of bases and so forth.

As used herein, the term "hydrocarbon-based," "hydrocarbon-based substituent" and the like denotes a substituent having a carbon directly attached to the remainder of the molecule and having predominantly hydrocarbyl character within the context of this invention.

Examples of hydrocarbyl substituents which might be useful in connection with the present invention include the following:

(1) hydrocarbon substituents, that is, aliphatic (e.g., alkyl or alkenyl), alicyclic (e.g., cycloalkyl, cycloalkenyl) substituents, aromatic, aliphatic and alicyclic-substituted aromatic nuclei and the like as well as cyclic substituents wherein the ring is completed through another portion of the molecule (that is, for example, any two indicated substituents may together form an alicyclic radical);

(2) substituted hydrocarbon substituents, that is, those substituents containing nonhydrocarbon radicals which, in the context of this invention, do not alter the predominantly hydrocarbon substituent; those skilled in the art will be aware of such radicals (e.g., halo (especially chloro and fluoro), hydroxy, alkoxy, mercapto, alkylmercapto, nitro, nitroso, sulfoxy, etc.);

(3) hetero substituents, that is, substituents which will, while having predominantly hydrocarbyl character within the context of this invention, contain other than carbon present in a ring or chain otherwise composed of carbon atoms. Suitable heteroatoms will be apparent to those of ordinary skill in the art and include, for example, sulfur, oxygen, nitrogen and such substituents as, e.g., pyridyl, furyl, thienyl, imidazolyl, etc., are exemplary of these hereto substituents. Heteroatoms and preferably no more than one, will be present for each ten carbon atoms in the hydrocarbon-based substituents. Typically, there will be no such radicals or heteroatoms in the hydrocarbon-based substituent and it will, therefore, be purely hydrocarbon.

The hydroxyalkane phosphonic acids of the present invention are defined by the following general formula:

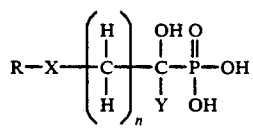

wherein X is oxygen, sulfur or a secondary amino group; n is an integer from 1 to 8; Y is hydrogen or a phosphonic acid group; and R is an alkyl group having from 1 to about 100 carbon atoms. R is also useful when it is an alkyl group containing from 1 to about 30 carbon atoms. R is preferably an alkyl group having from about 6 to about 4 carbon atoms, most preferably about 8 to about 18 carbon atoms; Y is a phosphonic acid group; n is an integer from 2 to 4, most preferably 3; and X is oxygen or sulfur, most preferably sulfur.

The preparation of the hydroxyalkane phosphonic acids occurs by the reaction of a carboxylic acid with phosphorous acid and phosphorus trichloride. The carboxylic acid has an oxygen atom, sulfur atom or secondary amino group in the main backbone of the carboxylic acid. The carboxylic acid is added to a flask and heated to 70° to 150° C. Phosphorous acid is added to the reaction. Phosphorus trichloride is then added dropwise to the reaction, and the reaction is continued until no more hydrogen chloride is evolved. Usually the reaction takes from 1 to 4 hours.

EXAMPLE A-1

Add 1420 parts of 1-decene to 921 parts of mercapto acetic acid. The reaction is exothermic and raises the temperature to around 80° C. Add dropwise 4 parts of a 60% solution of benzoyl peroxide and maintain the reaction at around 90° C. to 110° C. for 4 hours. When infrared analysis shows that most of the olefin has reacted, cool the reaction to ambient temperature and add 600 parts xylene and 1100 parts phosphorous acid to the reaction. Heat the mixture to 90° to 110° C. and add 913 parts of phosphorus trichloride dropwise over 4 hours. Hold the reaction mixture at 110° C. for 4 hours. The reaction is complete when the hydrogen chloride ceases to evolve.

EXAMPLE B-1

Add 842 parts of Armeen Z (this is a nitrogen-containing carboxylic acid from Armak Chemical Corporation) and 600 parts of xylene to a reaction vessel. Heat the mixture to around 110° C. and add 164 parts of phosphorous acid. Next add 137 parts of phosphorus trichloride dropwise. Heat the reaction to 120° C. and hold for 4 hours. The cessation of hydrogen chloride evolution is the end of the reaction.

EXAMPLE C-1

Add 1128 parts of an dodecylthiopropionic acid, 870 parts xylene and 420 parts of phosphorous acid to a reaction vessel. Heat the mixture to 110° C. and add 351 parts of phosphorus trichloride over 4 hours. Heat the reaction mixture to 130° C. and maintain the temperature for 4 hours. When the evolution of hydrogen chloride ceases, the reaction is over.

The hydroxyalkane phosphonic acid of the present invention may be reacted with bases to form salts. The bases contemplated by the present invention are selected from the group consisting of:

(A) a detergent;
(B) a dispersant; and
(C) an amine represented by the following formula:

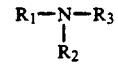

wherein $R_1$, $R_2$ and $R_3$ are each independently hydrogen or hydrocarbyl; and (D) mixtures thereof.

The detergents are overbased or neutral alkali, alkaline earth and transition metal salts of acidic components. wherein the metal is present in a stoichiometric excess to the acidic component.

In the present specification and claims the term "overbased" is used to designate materials containing a stoichiometric excess of metal cations relative to the anion portion of the molecule and is, therefore, inclusive of those materials which have been referred to in the art as overbased, superbased, hyperbased, etc., as discussed supra.

The terminology "metal ratio" is used to designate the ratio of the total chemical equivalents of the metal in the overbased material (e.g., a metal sulfonate or carboxylate) to the chemical equivalents of the metal in the product which would be expected to result in the reaction between the organic material to be overbased (e.g., sulfonic or carboxylic acid) and the metal-containing reactant (e.g., calcium hydroxide, barium oxide, etc.) according to the known chemical reactivity and stoichiometry of the two reactants.

It is desirable that the overbased materials used to prepare the disperse system have a metal ratio of at least about 3.5 and preferably about 4.5. An especially suitable group of the preferred sulfonic acid overbased materials has a metal ratio of at least about 7.0 While overbased materials having a metal ratio of 75 have been prepared, normally the maximum metal ratio will not exceed about 30 and, in most cases, not more than about 20.

Generally, these overbased materials are prepared by treating a reaction mixture comprising the organic material to be overbased, a reaction medium consisting essentially of at least one inert, organic solvent for said organic material, a stoichiometric excess of a metal base, and a promoter with an acidic material. The methods for preparing the overbased materials as well as an extremely diverse group of overbased materials are well known in the prior art.

Materials which can be overbased are generally oil-soluble organic acids including phosphorus acids, thiophosphorus acids, sulfur acids, carboxylic acids, thiocarboxylic acids, and the like, as well as the corresponding alkali and alkaline earth metal salts thereof.

For reasons of economy and performance, overbased oil-soluble carboxylic and sulfonic acids are particularly suitable. Illustrative of the carboxylic acids are palmitic acid, stearic acid, oleic acid, linoleic acid, behenic acid, polyisobutene (M.W.—5000)-substituted succinic acid, polypropylene (M.W.—10,000)-substituted succinic acid, mixtures of these acids, their alkali and alkaline earth metal salts, and/or their anhydrides. Of the oil-soluble sulfonic acids, the mono-, di-, and trialiphatic hydrocarbon substituted aryl sulfonic acids and the petroleum sulfonic acids (petrosulfonic acids) are particularly preferred. Illustrative examples of suitable sulfonic acids include mahogany sulfonic acids, petrolatum sulfonic acids, dodecylbenzene sulfonic acids, dinonylbenzene sulfonic acids, the sulfonic acid derived by the treatment of polyisobutene having a molecular weight of 1500 with chlorosulfonic acid, paraffin wax sulfonic acid, polyethylene (M.W.—750) sulfonic acids, etc. Obviously, it is necessary that the size and number of aliphatic groups on the aryl sulfonic acids be sufficient to render the acids soluble or dispersible in oil. Normally the aliphatic groups will be alkyl and/or alkenyl groups such that the total number of aliphatic carbons is at least twelve.

The metal compounds used in preparing the overbased materials are normally the basic salts of metals in Group I-A and Group II-A of the Periodic Table although other metals such as lead, zinc, manganese, etc. can be used in the preparation of overbased materials. Preferred metals are calcium, barium, magnesium, sodium and potassium, with calcium, magnesium and sodium most preferred. The anionic portion of the salt can be hydroxyl, oxide, carbonate, hydrogen carbonate, nitrate, sulfite, hydrogen sulfite, halide, amide, sulfate, etc. For purposes of this invention the preferred overbased materials are prepared from the alkali or alkaline earth metal oxides, hydroxides, and alcoholates such as the lower alkoxides.

The promoters, that is, the materials which permit the incorporation of the excess metal into the overbased material, are also quite diverse and well known in the art. These include the alcoholic and phenolic promoters which are preferred. The alcoholic promoters include the alkanols of one to about twelve carbon atoms such as methanol, ethanol, amyl alcohol, octanol, isopropanol, and mixtures of these and the like. Phenolic promoters include a variety of hydroxy-substituted benzenes and naphthalenes.

Included within the known group of useful acidic materials are liquid acids such as formic acid, acetic acid, nitric acid, sulfuric acid, hydrochloric acid, hydrobromic acid, carbamic acid, substituted carbamic acids, etc. Acetic acid is a very useful acidic material although inorganic acidic materials such as HCl, SO, $SO_3$, $CO_2$, $H_2S$, $N_2O_3$, etc., are ordinarily employed as the acidic materials. The most preferred acidic materials are carbon dioxide and acetic acid.

The temperature at which the acidic material is contacted with the remainder of the reaction mass depends to a large measure upon the promoting agent used. With a phenolic promoter, the temperature usually ranges from about 80° C. to 300° C., and preferably from about 100° C. to about 200° C. When an alcohol or mercaptan is used as the promoting agent, the temperature usually will not exceed the reflux temperature of the reaction mixture and preferably will not exceed about 100° C.

EXAMPLE A-2

Heat a reaction mixture of 1305 grams of calcium sulfonate having a metal ratio of 2.5 dissolved in mineral oil, 220 grams of methyl alcohol, 72 grams of isobutanol, and 38 grams of n-phentanol to 35° C. Subject the reaction mixture to the following operating cycle four times; mixing with 143 grams of 90% calcium hydroxide and treating the mixture with carbon dioxide until it has a base number of 32–39. Heat the resulting product to 155° C. during a period of 9 hours to remove the alcohols and then filter it this temperature. The filtrate is a calcium overbased petrosulfonate having a metal ratio of 12.2. The overbased materials used in the present invention are known in the art and examples are described in U.S. Pat. No. 3,492,231, column 7, line 47 through column 12, line 58, (herein incorporated by reference for disclosure of overbased metal salts).

The hydroxyalkane phosphonic acids of the present invention may also be reacted with a dispersant. The dispersant is selected from the group consisting of:
(A) Mannich dispersants;
(B) Succinimide dispersants;
(C) Nitrogen-containing ester type dispersants; and
(D) Dispersant-viscosity improvers.

(A) Mannich Dispersants

Mannich dispersants are formed by the reaction product of an aldehyde, an amine and hydroxyaromatic compound. The reaction may occur from room temperature to about 225° C., usually 50°–200° C. (75°–125° C. most preferred), with the amounts or reagent being such that the molar ratio of hydroxyaromatic compound to formaldehyde to amine is in the range from about 1:1:1 to about 1:3:3.

The first reagent is a hydroxyaromatic compound. This term includes phenols (which are preferred), carbon-, oxygen-, sulfur- and nitrogen-bridged phenols and the like
as well as phenols directly linked through covalent bonds (e.g. 4,4'-bis(hydroxy)biphenyl), hydroxy compounds derived from fused-ring hydrocarbon (e.g., naphthols and the like); and polyhydroxy compounds such as catechol, resorcinol and hydroquinone. Mixtures of one or more hydroxyaromatic compounds can be used as the first reagent.

The hydroxyaromatic compounds are those substituted with at least one, and preferably not more than two, aliphatic or alicyclic substituents having at least about 6 (usually at least about 30, more preferably at least 50) carbon atoms and up to about 7000 carbon atoms. Examples of such substituents derived from polymerization of olefins such as ethylene, propylene, 1-butene, 2-butene, isobutene and the like. Both homopolymers (made from a single olefin monomer) and interpolymers (made from two or more of olefin monomers) can serve as sources of these substituents and are encompassed in the term "polymers" as used herein. Substituents derived from polymers of ethylene, propylene, 1-butene and isobutene are preferred, especially those containing at least about 30 and preferably at least about 50 aliphatic carbon atoms.

The aliphatic and alicyclic substituents as well as the aryl nuclei of the hydroxyaromatic compound are generally described as "hydrocarbon-based" substituents.

As used herein, the term "hydrocarbon-based substituent" denotes a substituent having a carbon atom directly attached to the remainder of the molecule and having predominantly hydrocarbyl character within the context of this invention.

Preferably, the hydrocarbon-based substituent in the compositions of this invention are free from acetylenic unsaturation. Ethylenic unsaturation, when present, preferably will be such that no more than one ethylenic linkage will be present for every 10 carbon-to-carbon bonds in the substituent. The substituents are usually preferably hydrocarbon in nature and more preferably, substantially saturated hydrocarbon. As used in this specification, the word "lower" denotes substituents, etc. containing up to seven carbon atoms; for example, lower alkoxy, lower alkyl, lower alkenyl, lower aliphatic aldehyde.

Introduction of the aliphatic or alicyclic substituent onto the phenol or other hydroxyaromatic compound is usually effected by mixing a hydrocarbon (or a halogenated derivative thereof, or the like) and the phenol at a temperature of about 50°–200° C. in the presence of a suitable catalyst, such as aluminum trichloride, boron trifluoride, zinc chloride or the like. See, for example, U.S. Pat. No. 3,368,972 which is incorporated by reference for its disclosures in this regard. This substituent can also be introduced by other alkylation processes known in the art.

Especially preferred as the first reagent are monosubstituted preferred as the first reagent are monosubstituted phenols of the general formula:

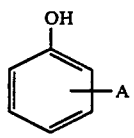

wherein A is an aliphatic or alicyclic hydrocarbon-based substituent of Mn (V.P.O.) of about 420 to about 10,000.

The second reagent is a hydrocarbon-based aldehyde, preferably a lower aliphatic aldehyde. Suitable aldehydes include formaldehyde, benzaldehyde, acetaldehyde, the butyraldehydes, hydroxybutyraldehydes and heptanals, as well as aldehyde presursors which react as aldehydes under the conditions of the reaction such as paraformaldehyde, paraldehyde, formalin and methal. Formaldehyde and its polymers (e.g., paraformaldehyde, trioxane) are preferred. Mixtures of aldehydes may be used as the second reagent.

The third reagent is a compound containing an amino group having at least one hydrogen atom directly bonded to amino nitrogen. Suitable amino compounds are those containing only primary, only secondary, or both primary and secondary amino groups, as well as polyamines in which all but one of the amino groups may be tertiary. Suitable amino compounds include ammonia, aliphatic amines, aromatic amines, heterocyclic amines and carboxylic amines, as well as polyamines such as alkylene amines, arylene amines, cyclic polyamines and the hydroxy-substituted derivatives of such polyamines. Mixtures of one or more amino compounds can be used as the third agent.

Such amines include, for example, mono- and di-alkyl-substituted amines, mono- and di-alkenyl-substituted amines, and amines having one N-alkenyl substituent and one N-alkyl substituent and the like. The total number of carbon atoms in these aliphatic monoamines will, as mentioned before, normally not exceed about 40 and usually not exceed about 20 carbon atoms. Specific examples of such monoamines include ethylamine, diethylamine, n-butylamine.

Hydroxyamines both mono- and polyamines are also useful as (a) provided they contain at least one primary or secondary amino group. Examples of such hydroxy-substituted amines include ethanolamine, diethanolamine, and N-(hydroxypropyl)-propylamine.

Another group of amines suitable for use as (a) are branched polyalkylene polyamines.

These reagents may be expressed by the formula:

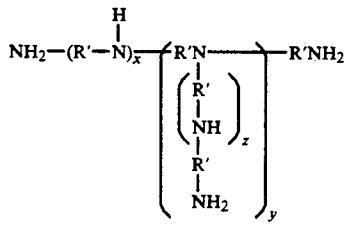

wherein R' is an alkylene group such as ethylene, propylene, butylene and other homologues (both straight chained and branched), etc., but preferably ethylene; and x, y and z are integers, x being for example, from 4 to 24 or more but preferably 6 to 18, y being for example 1 to 6 or more but preferably 1 to 3, and z being for example 0–6 but preferably 0–1. The x and y unites may be sequential, alternative, orderly or randomly distributed.

The most preferred amines are the alkylene polyamines, including the polyalkylene polyamines, as described in more detail hereafter. The alkylene polyamines include those conforming to the formula:

wherein b is from 1 to about 10, each R" is independently a hydrogen atom, a hydrocarbyl group or a hydroxy-substituted hydrocarbyl group having up to about 30 atoms, and the "Alkylene" group has from about 1 to about 10 carbon atoms but the preferred alkylene is ethylene or propylene. Especially preferred are the alkylene polyamines where each R" is hydrogen with the ethylene polyamines and mixtures of ethylene polyamines being the most preferred. Usually b will have an average value of from about 2 to about 7. Such alkylene polyamines include methylene polyamine, ethylene polyamines, butylene polyamines, propylene polyamines, pentylene polyamines, hexylene polyamines, heptylene polyamines, etc. The higher homologs of such amines and related amino-alkyl-substituted piperazines are also included.

Ethylene polyamines are especially useful for reasons of cost and effectiveness. Such polyamines are described in detail under the heading "Diamines and Higher Amines" in The Encyclopedia of Chemical Technology, Second Edition, Kirk and Othmer, Volume 7, pages 27-39, Interscience Publishers, Division of John Wiley and Sons, 1965, which is hereby incorporated by reference for their disclosure of useful polyamines.

Hydroxyalkyl alkylene polyamines having one or more hydroxyalkyl substituents on the nitrogen atoms are also useful. Preferred hydroxyalkyl-substituted alkylene polyamines are those in which the hydroxyalkyl group is a lower hydroxyalkyl group, i.e., having less than eight carbon atoms. Examples of such hydroxyalkyl-substituted polyamines include N-(2-hydroxyethyl-)ethylene diamine, N,N-bis(2-hydroxyethylehtylene diamine, 1-(2-hydroxyethyl)piperazine, monohydroxypropyl-substituted diethylene triamine, dihydroxypropyl-substituted tetraethylene pentamine.

EXAMPLE B-2

Heat a mixture of 1560 parts (1.5 equivalents) of a polyisobutylphenol having a molecular weight of about 885, 1179 parts of mineral oil and 99 parts of n-butyl alcohol to 80° C. under nitrogen, with stirring, and add 12 parts (0.15 equivalent) of 50% aqueous sodium hydroxide solution. Stir the mixture for 10 minutes and add 99 parts (3 equivalents) of paraformaldehyde. Stir the mixture at 80°-88° C. for 1.75 hours and then neutralize by the addition of 9 parts (0.15 equivalent) of acetic acid.

To the intermediate thus obtained add at 88° C., with stirring, 172 parts (4.2 equivalents) of a commercial polyethylene polyamine mixture containing about 3-7 nitrogen atoms per molecule and about 34.5% by weight nitrogen. Heat the mixture over about 2 hours to 150° C. and stir at 150°-160° C. for 3 hours, with volatile material being removed by distillaticn. Strip the remainder of the volatiles at 160° C./30 torr, and filter the residue at 150° C., using a commercial filter aid material, to yield the desired product as a filtrate in the form of 60% solution in mineral oil containing 1.95% nitrogen.

EXAMPLE C-2

Prepare a tetrapropylene substituted phenolformaldehyde intermediate by a method similar to that described in Example B-2. Heat a mixture of 393 parts (1 equivalent) of that intermediate, 168 parts (2 equivalents) of dicyandiamide, 250 parts of isopropyl alcohol and 458 parts of mineral oil to reflux and maintain at that temperature for about 9 hours. Remove volatiles by vacuum stripping and filter the residual liquid using a filter aid material. The filtrate is the desired product as a 50% solution in mineral oil containing 4.41% nitrogen.

Mannnich dispersants are described in the following patents: U.S. Pat. No. 3,980,569; U.S. Pat. No. 3,877,899; and U.S. Pat. No. 4,454,059 (herein incorporated by reference for their disclosure to Mannich dispersants).

(B) Succinimide Dispersants

Succinimide dispersants are prepared by the reaction product of a carboxylic acid acylating agent with an amine.

The acylating agents used in making the derivatives of the present invention are well known to those skilled in the art and have been found to be useful as additives for lubricants and fuels and as intermediates for preparing the same. See, for example, the following U.S. Patents which are hereby incorporated by reference for their disclosures relating to the preparation of carboxylic acid acylating agents: U.S. Pat. Nos. 3,219,666; 3,272,746; 3,381,102; 3,254,025; 3,278,550; 3,288,714; 3,271,310; 3,373,111; 3,346,354; 3,272,743; 3,374,174; 3,307,928; and 3,394,179.

Generally, these carboxylic acid acylating agents are prepared by reacting an olefin polymer or chlorinated analog thereof with an unsaturated carboxylic acid or derivative thereof such as acrylic acid, fumaric acid, maleic anhydride and the like. Typically, these acylating agents are polycarboxylic acylating agents such as the succinic acid acylating agents derived from maleic acid, its isomers, anhydride and chloro and bromo derivatives. A dicarboxylic acid in the form of a succinic acid derivative is the preferred acylating agent (A).

These acylating agents have at least one hydrocarbyl-based substituent of about 20 to about 500 carbon atoms. Generally, this substituent has an average of at least about 30, and often at least about 50 carbon atoms. Typically, this substituent has a maximum average of about 300, and often about 200 carbon atoms.

In general, the hydrocarbon-based substituents of at least about 20 carbon atoms present in the acylating agents used in this invention are free from acetylenic unsaturation; ethylenic unsaturation, when present will generally be such that there is not more than one ethylenic linkage present for every ten carbon-to-carbon bonds in the substituent.

As noted above, the hydrocarbon-based substituents present in the acylating agents of this invention are derived from olefin polymers or chlorinated analogs thereof. The olefin monomers from which the olefin polymers are derived are polymerizable olefins and monomers characterized by having one or more ethylenic unsaturated group. They can be monoolefinic monomers such as ethylene, propylene, butene-1, isobutene and octene-1 or polyolefinic monomers (usually di-olefinic monomers such as butadiene-1,3 and isoprene). Usually these monomers are terminal olefins, that is, olefins characterized by the presence of a double bond at the end of the monomer. However, certain internal olefins can also service as monomers (these are sometimes referred to as medial olefins). When such medial olefin monomers are used, they normally are employed in combination with terminal olefins to produce olefin polymers which are interpolymers.

Generally the olefin polymers are homo- or interpolymers of terminal hydrocarbyl olefins of about 2 to about 16 carbon atoms. A more typical class of olefin polymers is selected from that group consisting of homo- and interpolymers of terminal olefins to two to six carbon atoms, especially those of two to four carbon atoms.

Often the olefin polymers are poly(isobutene)s. As indicated above, polyisobutenyl substituents are used preferably in connection with the present invention. These polyisobutenyl polymers may be obtained by polymerization of a C$_4$ refinery stream having a butene content of about 35 to about 75 percent by weight and an isobutene content of about 30 to about 60 percent by weight in the presence of a Lewis acid catalyst such as aluminum chloride or boron trifluoride. These poly(isobutene)s contain predominantly (that is, greater than 80% of the total repeat units) isobutene repeat units of the configuration

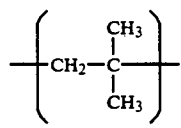

Typically, the hydrocarbon-based substituent in the carboxylic acid acylating agent as used in the present invention is a hydrocarbyl, alkyl or alkenyl group of about 30, often about 50, to about 500, sometimes about 300, carbon atoms. For convenience herein, such substituents are represented by the indicia "hyd."

As noted above, typical acylating agents (A) used in making the derivatives of this invention are substituted succinic acids or derivatives thereof. In this case, the preferred acylating agent (A) can be represented by the formulae:

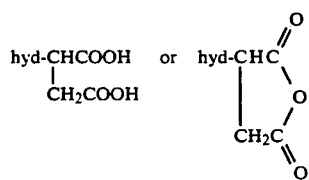

Such succinic acid acylating agents can be made by the reaction of maleic anhydride, maleic acid, or fumaric acid with the afore-described olefin polymer, as is shown in the patents referred to above. Generally, the reaction involves merely heating the two reactants at a temperature of about 150° to about 200°. Mixtures of these polymeric olefins, as well as mixtures of these unsaturated mono- and polycarboxylic acids can also be used.

The monoamines and polyamines useful must be characterized by the presence within their structure of at least one H—N group. Therefore, they have at least one primary or secondary amino group. The amines can be aliphatic, cycloaliphatic, aromatic, or heterocyclic. The amines may be saturated or unsaturated. If unsaturated, the amine will be free from acetylenic unsaturation. The amines may also contain non-hydrocarbon substituents or groups as long as these groups do not significantly interfere with the reaction of the amines with the acylating reagents of this invention. Such non-hydrocarbon substituents or groups include lower alkoxy, lower alkyl mercapto, nitro, interrupting groups such as —O— and —S— (e.g., as in such groups as —CH$_2$CH$_2$—X—CH$_2$CH$_2$— where X is —O— or —S—). The description of amines (see Mannich dispersants) is hereby incorporated.

EXAMPLE D-2

Heat a mixture of 510 parts (0.28 mole) of polyisobutene (Mn=1845; Mw=5325) and 59 parts (0.590 mole) of maleic anhydride to 110° C. Heat this mixture to 190° C. in seven hours adding 43 parts (0.6 mole) of gaseous chlorine beneath the surface. Add at 190°-192° C. an additional 11 parts (0.16 mole) of chlorine over 3.5 hours. Strip the reaction mixture stripped by heating at 190°-193° C. with nitrogen blowing for 10 hours. The residue is the desired polyisobutene-substituted succinic acylating agent having a saponification equivalent number of 87 as determined by ASTM procedure D-94.

EXAMPLE E-2

Prepare a mixture by the addition of 10.2 parts (0.25 equivalent) of a commercial mixture of ethylene polyamines having from about 3 to about 10 nitrogen atoms per molecule to 113 parts of mineral oil and 161 parts (0.25 equivalent) of the substituted succinic acylating agent of Example D-2 at 138° C. Heat the reaction mixture is heated to 150° C. in 2 hours and strip by blowing with nitrogen. The reaction mixture is filtered to yield the filtrate as an oil solution of the desired product.

EXAMPLE F-2

Prepare a polyisobutenyl succinic anhydride by the reaction of a chlorinated polyisobutylene with maleic anhydride at 200° C. The polyisobutenyl radical has an average molecular weight of 850 and the resulting alkenyl succinic anhydride is found to have an acid number of 113 (corresponding to an equivalent weight of 500). Add to a mixture of 500 grams (1 equivalent) of this polyisobutenyl succinic anhydride and 160 grams of toluene at room temperature 61 grams (1.5 equivalent) of mixed polyamine. Make the addition portionwise throughout a period of 15 minutes, and an initial exothermic reaction caused the temperature to rise to 50° C. Heat the mixture and distill a water-toluene azeotrope from the mixture. When no more water will distill, heat the mixture to 150° C. at reduced pressure to remove the toluene. By diluting the residue with 350 grams of mineral oil this solution will be found to have a nitrogen content of 1.6%.

A description of succinimide dispersants occurs in U.S. Pat. No. 3,172,892 and U.S. Pat. No. 4,234,435 (herein incorporated by reference for their disclosure of succinimide dispersants).

(C) Nitrogen-containing Ester Type Dispersants

The nitrogen-containing ester type dispersant is commonly formed by the reaction product of a carboxylic acid acylating agent reacted with a polyol alcohol and that reaction product further reacted with an amine source. The esters of this invention are those of the above-described carboxylic acid acylating agents with hydroxy compounds which may be aliphatic compounds such as monohydric and polyhydric alcohols or aromatic compounds such as phenols and naphthols.

The alcohols from which the esters may be derived preferably contain up to about 40 aliphatic carbon atoms. They may be monohydric alcohols such as methanols, ethanol, isoctanol, dodecanol, cyclohexanol, cyclopentanol, behenyl alcohol, hexatricontanol, neopentyl alcohol, isobutyl alcohol and benzyl alcohol. The polyhydric alcohols preferably contain from 2 to about 10 hydroxy radicals. They are illustrated by, for example, ethylene glycol, diethylene glycol, triethylene glycol, tetraethylene glycol, and other alkylene glycols in which the alkylene radical contains from 2 to about 8 carbon atoms. Other useful polyhydric alcohols include glycerol, mono-oleate of glycerol, monostearate of glycerol and monomethyl ether of glycerol.

An especially preferred class of polyhydric alcohols are those having at least three hydroxy radicals, some of which have been esterified with a monocarboxylic acid having from about 8 to about 30 carbon atoms such as octanoic acid, oleic acid, stearic acid, linoleic acid, dodecanoic acid, or tall oil acid. Examples of such partially esterified polyhydric alcohols are the mono-oleate of sorbitol, distearate of sorbitol, mono-oleate of glycerol, monostearate of glycerol, di-dodecanoate of erythritol.

Still other classes of the alcohols capable of yielding the esters of this invention comprises the ether-alcohols and amino-alcohols including, for example, the oxyalkylene-, oxy-arylene-, amino-alkylene-, and amino-arylene-substituted alcohols having one or more oxy-alkylene, amino-alkylene or amino-arylene oxy-arylene radicals.

The carboxylic acid acylating agents have been fully described above (see (B) Succinimide Dispersants). The disclosure for these agents is hereby incorporated. The amines have been fully described above (see (A) Mannich Dispersants). The disclosure for the amines is hereby incorporated.

The esters of this invention may be prepared by one of several methods. The method which is preferred because of convenience and superior properties of the esters it produces, involves the reaction of a suitable alcohol or phenol with a substantially hydrocarbon-substituted succinic anhydride. The esterification is usually carried out at a temperature above about 100° C., preferably between 150° C. and 300° C.

A substantially hydrocarbon-substituted succinic anhydride is prepared by chlorinating a polyisobutene having a molecular weight of 1000 to a chlorine content of 4.5% and then heating the chlorinated polyisobutene with 1.2 molar proportions of maleic anhydride at a temperature of 150°-220° C. The succinic anhydride thus obtained has an acid number of 130. A mixture of 874 grams (1 mole) of the succinic anhydride and 104 grams (1 mole) of neopentyl glycol is mixed at 240°-250° C./30 mm. for 12 hours. The residue is a mixture of the esters resulting from the esterification of one and both hydroxy radicals of the glycol. It has a saponification number of 101 and an alcoholic hydroxyl content of 0.2%. Commonly, the reaction occurs between a polyisobutylene succinic anhydride, pentaerythritol and a polyamine. An example of this dispersant is shown in U.S. Pat. No. 3,381,022 (herein incorporated by reference for its disclosure to the nitrogen-containing ester type dispersant).

(D) Dispersant-Viscosity Improvers

The dispersant-viscosity improvers of the present invention are polymers backbone which are functionalized by reacting with an unsaturated carboxylic acid reagent. A true or normal block copolymer or a random block copolymer, or combinations of both are utilized. They are hydrogenated before use in this invention so as to remove virtually all of their olefinic double bonds. Techniques for accomplishing this hydrogenation are well known to those of skill in the art and need not be described in detail at this point. Briefly, hydrogenation is accomplished by contacting the copolymers with hydrogen at superatmospheric pressures in the presence of a metal catalyst such as colloidal nickel, palladium supported on charcoal, etc.

In general, it is preferred that these block copolymers, for reasons of oxidative stability, contain no more than about 5 percent and preferably no more than about 0.5 percent residual olefinic unsaturation on the basis of the total number of carbon-to-carbon covalent linkages within the average molecule. Such unsaturation can be measured by a number of means well known to those of skill in the art, such as infrared, NMR, etc. Most preferably, these copolymers contain no discernible unsaturation, as determined by the aforementioned analytical techniques.

The block copolymers typically have number average molecular weights in the range of about 10,000 to about 500,000 preferably about 30,000 to about 200,000. The weight average molecular weight for these copolymers is generally in the range of about 50,000 to about 500,000, preferably about 30,000 to about 300,000.

The unsaturated carboxylic reagent generally contains an alpha-beta olefinic unsaturation. By the term alpha-beta olefinic unsaturated carboxylic acid reagent, it is meant to include alpha-beta olefinic unsaturated carboxylic acids per se and functional derivatives thereof, such as anhydrides, esters, amides, imides, salts, acyl halides, and nitriles. These carboxylic acid reagents may be either monobasic or polybasic in nature. When they are polybasic they are preferably dicarboxylic acids, although tri- and tetracarboxylic acids can be used. Exemplary of the monobasic alpha-beta olefinic unsaturated carboxylic acid reagents are the carboxylic acids corresponding to the formula:

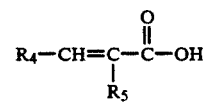

wherein $R_4$ is hydrogen, or a saturated aliphatic or alicyclic, aryl, alkylaryl or heterocyclic group, preferably hydrogen or a lower alkyl group, and $R_5$ is hydrogen or a lower alkyl group. By lower alkyl it is meant from 1 to about 10 carbon atoms. The total number of carbon atoms in $R_4$ and $R_5$ should not exceed 18 carbon atoms. Specific examples of useful monobasic alpha-beta olefinic unsaturated carboxylic acids are acrylic acid, methacrylic acid, cinnamic acid, crotonic acid, 2-phenylpropenoic acid, etc. Exemplary polybasic acids include maleic acid, fumaric acid, mesaconic acid, itaconic acid and citraconic acid.

The alpha-beta olefinic unsaturated reagents also include functional derivatives of the foregoing acids, as noted. These functional derivatives include the anhydrides, esters, amides, imides, salts, acid halides, and nitriles and other nitrogen containing compounds of the aforedescribed acids. A preferred alpha-beta olefinic unsaturated carboxylic acid reagent is maleic anhydride.

More specifically, such amine functional derivatives of the alpha-beta olefinic unsaturated reagent can have the formula:

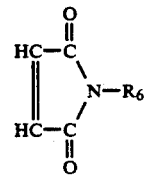

or

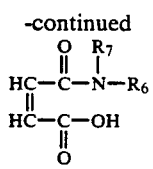

wherein R$_6$ and R$_7$, independently, can be hydrogen, an alkyl having from about 1 to about 12 carbon atoms and preferably from about 1 to about 6 carbon atoms, an alkyl substituted aromatic having from about 7 to about 12 carbon atoms and preferably from about 7 to about 9 carbon atoms, or a moiety containing N, 0 or S as heteroatoms. Examples of highly preferred compounds include N-(3,6-dioxaheptyl)maleimide, N-(3-dimethylaminopropyl)-maleimide, and N-(2-methoxyethoxyethyl)maleimide.

Primary amine-containing compounds of the present invention can broadly be represented by the formula R-NH$_2$ where R is hydrogen, an alkyl, a cycloalkyl, an aromatic, and combinations thereof, e.g., an alkyl substituted cycloalkyl. Furthermore, R$_8$ can be an alkyl, an aromatic, a cycloalkyl group, or combination thereof containing one or more secondary or tertiary amine groups therein. R$_8$ can also be an alkyl, a cycloalkyl, an aromatic group, or combinations thereof containing one or more heteroatoms (for example oxygen, nitrogen, sulfur, etc.). R$_8$ can further be an alkyl, a cycloalkyl, an aromatic, or combinations thereof containing sulfide or oxy linkages therein. Generally, R$_8$ is hydrogen or said various R groups containing from 1 to about 25 carbon atoms with from about 1 to about 6 or 7 carbon atoms being desirable. Exemplary of such primary amine-containing compounds are the following wherein R$_8$ is as set forth immediately herein above: ammonia, N,N-dimethylhydrazine, methylamine, ethylamine, butylamine, 2-methoxyethylamine, N,N-dimethyl-1,3-propanediamine, N-ethyl-N-methyl-1, 3-propanediamine, N-methyl-1,3-propanediamine, N-(3-aminopropyl)morpholine, 3-alkoxypropylamines wherein the alkoxy group contains from 1 to 18 carbon atoms, usually an alkoxy group having from 1 to 8 carbon atoms and has the formula R$_9$—O—CH$_2$CH$_2$CH$_2$—NH$_2$, such as 3-methoxypropylamine, 3-isobutyoxypropylamine and 3-(alkoxypolyethoxy)-propylamines having the formula R$_{80}$(CH$_2$ CH$_2$O)$_x$CH$_2$CH$_2$CH$_2$NH$_2$ wherein the alkoxy group is as immediately set forth above and where x is 1 to 50, 4,7-dioxaoctylamine, N-(3-aminopropyl)-N$^1$-methyl-piperazine, N-(2-aminoethyl)piperazine, (2-aminoethyl)pyridines, aminopyridines, 2-aminoethylpyridines, 2-aminomethylfuran, 3-amino-2-oxotetrahydrofuran, N-(2-aminoethyl)pyrolidine, 2-aminomethylpyrrolidine, 1-methyl-2-aminomethylpyrrolidine, 1-aminopyrrolidine, 1-(3-aminopropyl)-2-methylpiperidine, 4-aminomethylpiperidine, N-(2-aminoethyl)morpholine, 1-ethyl-3-aminopiperidine, 1-aminopiperidine, N-aminomorpholine, and the like.

Of these compounds, N-(3-aminopropyl)morpholine and N-ethyl-N-methyl-1,3-propanediamine are preferred with N,N-dimethyl-1,3-propanediamine being highly preferred.

Another group of primary amine-containing compounds are the various amine terminated polyethers. A specific example of such a polyether is given by the formula:

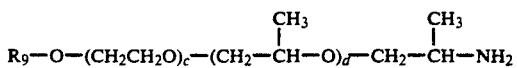

wherein c is from about 0 to about 50 with from about 5 to about 25 being preferred, d is from about 0 to about 35 with from about 2 to about 15 being preferred, and R$_9$ is an alkyl having from about 1 to about 18 carbon atoms.

EXAMPLE G-2

Charge a 1750 g sample of a hydrogenated styrene/-butadiene copolymer (BASF Glissoviscal CE5260) to a flask containing 5250 g mineral oil which and heat to 150° C. During this step and throughout the entire reaction sequence, maintain a N$_2$ blanket and mechanical stirring. Within 3 hours, obtain a homogeneous solution. Charge thirty-five (35 g) grams of maleic anhydride to the flask and dissolve thoroughly while increasing the reaction temperature to 160° C. Charge dropwise 14.1 g of the t-butyl peroxide initiator into the reaction mixture over 1 hour. Stir the solution at 160° C. for 1.5 additional hours. Charge the N$_2$ blanket to a subsurface purge (2.0 SCFH). Heat the reaction mixture to 170° C. and hold 2.0 hours to remove unreacted maleic anhydride and peroxide decomposition products. Infrared assay of the polymer solution will confirm the presence of succinic anhydride groups in the product.

EXAMPLE H-2

In a similar manner, prepare a reaction product utilizing Shellvis 40, a hydrogenated styrene-isoprene block copolymer produced by Shell Chemicals. The amount of Shellvis 40 is 10.0% by weight, the amount of maleic anhydride is 0.50 weight percent and the amount of neutral oil is 89.5 Weight percent. Charge these components to a flask in a manner as set forth in Example G-1 and heat while charging dropwise 0.5 weight percent of t-butyl peroxide over a period of 1 hour. Stir the solution at 160° C. for an additional 1.5 hours. Charge the nitrogen blanket to a subsurface purge. Heat the reaction mixture to 170° C. and hold for 2 hours to remove unreacted maleic anhydride and peroxide of composition products. Infrared assay of the polymer solution will confirm the presence of succinic anhydride groups in the product.

Often these polymers are grafted with a nitrogen-containing monomer or a monomer capable of reacting with an amine, i.e., maleic anhydride. Examples of dispersant-viscosity improvers are given in the following references:

| | |
|---|---|
| EP 171,167 | 3,687,905 |
| 3,687,849 | 4,670,173 |
| 3,756,954 | 4,320,012 |
| 4,320,019 | |

(herein incorporated by reference for their disclosure to dispersant-viscosity improvers).

The amines capable of reacting with the hydroxyalkane phosphonic acids of the present invention are represented by the following formula:

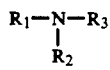

wherein $R_1$, $R_2$ and $R_3$ are each independently hydrogen, hydrocarbyl, or substituted hydrocarbyl. In a preferred embodiment, Rl is alkyl containing from 6 to 24 carbon atoms, most preferably 8 to 12, and $R_2$ is an alkyl radical containing 6 to 24 carbon atoms. In a second preferred embodiment $R_1$ is alkenyl and $R_2$ and $R_3$ are each independently hydrogen or hydrocarbyl. Preferably $R_1$ is alkenyl having about 6-24 carbon atoms and $R_2$ and $R_3$ are hydrogen. When $R_1$ is alkenyl, it may be sulfurized by techniques known in the art. Examples of amines used in the present invention are oleylamine, dioleylamine, Primene 81R (trialkyl amine having 12 to 14 carbon atoms in the alkyl group; available from Rohm & Haas Corporation) and Primene JMT (t-octadecylamine, available commercially from Rohm & Haas Corporation). In a third preferred embodiment, $R_1$, $R_2$ and $R_3$ are each independently hydrogen, alkyl, alkylhydroxy, or alkoxy groups, provided that at least one of $R_1$, $R_2$ or $R_3$ is an alkylhydroxy or alkoxy group. The preferred alkyl part of the alkylhydroxy and alkoxy groups is ethyl, propyl and butyl with ethyl preferred for the alkylhydroxy group and propyl preferred for the alkoxy group. When $R_1$, $R_2$ or $R_3$ is an alkoxy group, the amine is known as an ether amine. Examples of ether amine include but are not limited to hexyloxypropylamine, octyloxylpropylamine, tridecyloxypropylamine, dodecyloxyropropylamine and N-N-decyloxypropyl-1, 3-diamino propane. Ether amines are available commercially from Tomah Products, Inc. Examples of alkylhydroxyamines include but are not limited to N,N,N-(bis-hydroxyethyl)-octylamine, N,N,N-(bis-hydroxyethyl-dodecylamine, and N,N,N-(bis-hydroxymethyl)decylamine. The alkylhydroxyamines are available under the trade name Ethamines from Armak Company. In the above third embodiment, the alkyl, alkoxy and alkylhydroxy groups contain from 1 to about 30 carbon atoms, with about 6 to about 24 carbon atoms preferred and with about 8 to about 18 carbon atoms most preferred.

The hydroxyalkane phosphonic acids of the present invention may be reacted with the aforementioned bases or a combination of bases. For instance, the hydroxy phosphonic acid of the present invention may be reacted with a combination of overbased metal salts and basic nitrogen-containing dispersant.

The salts of the present invention are formed by the reaction of hydroxyalkane phosphonic acid with a base by mixing with agitation at a temperature between 25° C. and the decomposition temperature of the reactants. The acids and bases may be prepared by reacting the acid with base in the ratio of 1 equivalent acid to 1-20 equivalents of base. Preferably the ratio of equivalents of acid to equivalents of base is 1:1-4 with 1:1.3 most preferred.

The heteroatom containing hydroxyalkane phosphonic acid of the present invention may be used, in lubricants or in concentrates, by itself or in combination with any other known additive which includes, but is not limited to dispersants, detergents, antioxidants, antiwear agents, extreme pressure agents, emulsifiers, demulsifiers, friction modifiers, anti-rust agents, corrosion inhibitors, viscosity improvers, pour point depressants, dyes, and solvents to improve handleability which may include alkyl and/or aryl hydrocarbons. These additives may be present in various amounts depending on the needs of the final product.

Dispersants include but are not limited to hydrocarbon substituted succinimides, succinamides, esters, and Mannich dispersants as well as materials functioning both as dispersants and viscosity improvers. The dispersants listed above may be post-treated with reagents such as urea, thiourea, carbon disulfide, aldehydes, ketones, carboxylic acids, hydrocarbon substituted succinic anhydride, nitriles, epoxides, boron compounds, phosphorus compounds and the like.

Detergents include, but are not limited to Newtonian or non-Newtonian, neutral or basic salts of alkali, alkaline earth or transition metals with one or more hydrocarbyl sulfonic acid, carboxylic acid, phosphorus acid, thiophosphorus acid, dithiophosphorus acid, phosphinic acid, thiophosphinic acid, sulfur coupled phenol or phenol. Basic salts are salts that contain a stoichiometric excess of metal present per acid function.

Antioxidants, corrosion inhibitors, extreme pressure and antiwear agents include but are not limited to metal salts of a phosphorus acid, metal salts of a thio-phosphorus acid or dithiophosphorus acid; organic sulfides and polysulfides; chlorinated aliphatic hydrocarbons; phosphorus esters including dihydrocarbyl and trihydrocarbyl phosphites; boron-containing compounds including borate esters; and molybdenum compounds.

Viscosity improvers include but are not limited to polyisobutenes, polymethyacrylic acid esters, polyacrylic acid esters, diene polymers, polyalkyl styrenes, alkenyl aryl conjugated diene copolymers, polyolefins and multifunctional viscosity improvers.

Pour point depressants are a particularly useful type of additive often included in the lubricating oils described herein. See for example, page 8 of "Lubricant Additives" by C. V. Smalheer and R. Kennedy Smith (Lesius-Hiles Company Publishers, Cleveland, Ohio, 1967).

Anti-foam agents used to reduce or prevent the formation of stable foam include silicones or organic polymers. Examples of these and additional anti-foam compositions are described in "Foam Control Agents", by Henry T. Kerner (Noyes Data Corporation, 1976), pages 125–162.

These and other additives are described in greater detail in U.S. Pat. No. 4,582,618 (column 14, line 52 through column 17, line 16, inclusive), herein incorporated by reference for its disclosure of other additives that may be used in combination with the present invention.

The concentrate might contain 0.01 to 90% by weight of the hydroxyalkane phosphonic acids or salts. These acids or salts may be present in a final product, blend or concentrate in (in a minor amount, i.e., up to 50% by weight) any amount effective to act as an antiwear extreme pressure agent, but is preferably present in gear oils, greases, oil of lubricating viscosity, hydraulic oils, fuel oils or automatic transmission fluids in an amount of from about 0.5 to about 10%, preferably 1 to about 5% by weight. Often these materials are used in formulations betwen 0.015% to about 0.5%, preferably 0.025% to 0.2%, most preferably 0.025% to 0.15% by weight of phosphorous.

The phosphonic acids of the present invention may also be used in grease compositions.

Grease compositions or base grease stocks are derived from both mineral and synthetic oils. The synthetic oils include polyolefin oils (e.g., polybutene oil, decene oligomer, and the like), synthetic esters (e.g., dinonyl sebacate, trioctanoic acid ester of trimethylolpropane, and the like), polyglycol oils, and the like. The grease composition is then made from these oils by adding a thickening agent such as a sodium, calcium, lithium, or aluminum salts of fatty acids such as stearic acid. To this base grease stock, then may be blended the compounds of the present invention as well as other known or conventional additives. The grease composition may contain from about 0.1 weight percent to about 50 weight percent of the compounds of the present invention. As a preferred embodiment, the effective amount of the compounds in the grease composition will range from about 1.5 weight percent to about 25 weight percent, with 5-15 weight percent being most preferred.

Other additives which may optionally be present in the grease compositions and gear lubricants for use in this invention include:

Antioxidants, typically hindered phenols.

Surfactants, usually non-ionic surfactants such as oxyalkylated phenols and the like.

Corrosion, wear and rust inhibiting agents.

Friction modifying agents, of which the following are illustrative: alkyl or alkenyl phosphates or phosphites in which the alkyl or alkenyl group contains from about 10 to about 40 carbon atoms, and metal salts thereof, especially zinc salts; $C_{10-20}$ fatty acid amides; $C_{10-20}$ alkyl amines, especially tallow amines and ethoxylated derivatives thereof; salts of such amines with acids such as boric acid or phosphoric acid which have been partially esterified as noted above; $C_{10-20}$ alkyl-substituted imidazolines and similar nitrogen heterocycles.

The lubricating compositions and methods of this invention employ an oil of lubricating viscosity, including natural or synthetic lubricating oils and mixtures thereof. Natural oils include animal oils, vegetable oils, mineral lubricating oils, solvent or acid treated mineral oils, and oils derived from coal or shale. Synthetic lubricating oils include hydrocarbon oils, halo-substituted hydrocarbon oils, alkylene oxide polymers, esters of dicarboxylic acids and polyols, esters of phosphorus-containing acids, polymeric tetrahydrofurans and silicon-based oils.

Unrefined, refined and rerefined oils, either natural or synthetic may be used in the compositions of the present invention.

Specific examples of the oils of lubricating viscosity are described in U.S. Pat. No. 4,326,972 and European Pat. No. Publication 107,282, both herein incorporated by reference for their disclosures relating to lubricating oils. A basic, brief description of lubricant base oils appears in an article by D. V. Brock, "Lubricant Engineering", volume 43, pages 184-185, March, 1987. This article is herein incorporated by reference for its disclosures relating to lubricating oils.

A description of oils of lubricating viscosity occurs in U.S. Pat. No. 4,582,618 (column 2, line 37 through column 3, line 63, inclusive), herein incorporated by reference for its disclosure to oils of lubricating viscosity.

The following examples are provided so as to provide those of ordinary skill in the art with a complete disclosure and description of how to make the compounds and compositions of the invention and are not intended to limit the scope of what the inventors regard as their invention. Efforts have been made to insure accuracy with respect to numbers used (e.g. amounts, temperature, etc.) but some experimental errors and deviation should be accounted for. Unless indicated otherwise, parts are parts by weight, temperature is in degrees C, and pressure is at or near atmospheric.

TABLE 1

| Example | Acid | Amount | Base | Amount |
|---------|------|--------|------|--------|
| 1 | A-1 | 3066 | Primene JMT | 5653 |
| 2 | A-1 | 219 | F-2 | 1600 |
| 3 | A-1 | 438 | F-2, A-2 | 1600, 187 |
| 4 | A-1 | 219 | A-2 | 187 |
| 5 | B-1 | 738 | F-2 | 1182 |
| 6 | B-1 | 738 | A-2 | 187 |
| 7 | B-1 | 1476 | F-2 | 187 |
| 8 | B-1 | 738 | Primene JMT | 315 |
| 9 | C-1 | 2206 | Primene 81R | 823 |

In Table 1, references to the acids and bases are the corresponding example numbers. The procedure for the examples is as follows: mix the acid and base in a vessel with agitation and heat to 170° C. while blowing with nitrogen to remove water; cool the vessel to 100° C. and filter through diatomaceous earth.

Salts can be similarly prepared by reacting the acids of Examples A-1 through C-1 with one or more of the bases of Examples A-2 through H-2 or the amines described above.

Lubricating compositions may be prepared by adding from 0.05 to 10% of the products from Examples 1–9 to an oil.

Concentrate compositions containing from 0.05 to 90% by weight of the products of Examples 1–9 in oil.

A preferred embodiment of the present invention is the combination of the hydroxyalkane phosphoric acid salts with sulfur containing compounds which in lubricating formulations have shown improved antiwear and extreme pressure properties. Examples of sulfur containing compounds useful in the present invention are hydrocarbon polysulfides, sulfurized olefinic hydrocarbons and a sulfur compound characterized by the structural formula:

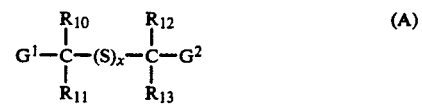

$$G^1-\underset{R_{11}}{\overset{R_{10}}{C}}-(S)_x-\underset{R_{13}}{\overset{R_{12}}{C}}-G^2 \qquad (A)$$

wherein $R_{10}$, $R_{11}$, $R_{12}$ and $R_{13}$ are each independently H or hydrocarbyl groups, or at least one of $R_{10}$ and $R_{12}$ is $G^1$ or $G^2$, or at least one combination of $R_{10}$ and $R_{11}$ or $R_{12}$ and $R_{13}$ together forms alkylene groups containing about 4 to about 7 carbon atoms;

$G^1$ and $G^2$ are each independently C(X)R, COOR, C≡N, $R_{14}C$≡$NR_{15}$, CON(R)$_2$ or NO$_2$, and $G^1$ also may be CH$_2$OH, wherein X is O or S, $R_{14}$ and each R is independently H or a hydrocarbyl group, $R_{15}$ is H or a hydrocarbyl group; or when both $G^1$ and $G^2$ are R C≡NR , the two $R_{15}$ groups together may be a hydrocarbylene group linking the two nitrogen atoms; or when $G^1$ is CH$_2$OH and $G^2$ is COOR, a lactone may be formed by intramolecular condensation of $G^1$ and $G^2$; and x is an integer from 1 to about 8.

$R_{10}$, $R_{11}$, $R_{12}$ and $R_{13}$ in Formula (A) are each independently hydrogen or hydrocarbyl groups. The hydrocarbyl groups may be aliphatic or aromatic groups such as alkyl, cycloalkyl, alkaryl, aralkyl or aryl groups. $R_{10}$ and $R_{11}$ and/or $R_{12}$ and $R_{13}$ together may be alkylene groups containing from about 4 to about 7 carbon atoms. In these embodiments, $R_{10}$ and $R_{11}$ together with the carbon atom bonded to $R_{10}$ and $R_{11}$ in Formula (A) will form a cycloalkyl group. Similarly, $R_{12}$ and $R_{13}$ together with the carbon atom bonded to $R_{12}$ and $R_{13}$ form a cycloalkyl group. Also, $R_{10}$ and/or $R_{12}$ may be $G^1$ or $G^2$.

The hydrocarbyl groups $R_{10}$, $R_{11}$, $R_{12}$ and $R_{13}$ in Formula (A) usually will contain up to about 30 carbon atoms. Preferably, the hydrocarbyl groups are alkyl groups containing up to about 10 carbon atoms. Specific examples of hydrocarbyl groups include methyl, ethyl, isopropyl, isobutyl, secondary butyl, cyclchexyl, cyclopentyl, octyl, dodecyl, octadecyl, etc.

The sulfur compounds of the present invention as represented by Formula (A) may be thia-aldehydes or thia-ketones. That is, $G^1$ and $G^2$ in Formula (A) are C(O)R groups. Various thia-bisaldehyde compounds are known, and the synthesis of such compounds have been described in the prior art such as in U.S. Pat. Nos. 3,296,137 and 2,580,695. Thia-aldehydes and thia-ketones are most conveniently prepared by the sulfurization of an aldehyde or a ketone.

Specific examples of thia-aldehydes and thia-ketones include compounds as represented by Formula (A) wherein $G^1$ and $G^2$ are C(O)R groups, x is 1 to 4 and $R_{10}$, $R_{11}$, $R_{12}$, $R_{13}$ and R are as follows:

| $R_{10}$ | $R_{11}$ | $R_{12}$ | $R_{13}$ | R |
| --- | --- | --- | --- | --- |
| $CH_3$ | H | $CH_3$ | H | H |
| $CH_3$ | $CH_3$ | $CH_3$ | $CH_3$ | $CH_3$ |
| $C_{25}$ | H | $C_2H_5$ | H | H |
| $CH_3C(O)-$ | H | $CH_3C(O)-$ | H | $CH_3$ |
| $CH_3C(O)-$ | H | $CH_3C(O)-$ | H | H |
| $C_2H_5$ | $C_4H_9$ | $C_2H_5$ | $C_4H_9$ | H |

When both $G^1$ and $G^2$ are C(O)R groups and $R_{10}$ and $R_{12}$ are H or hydrocarbyl groups, at least one R is a hydrocarbyl group.

The thia-aldehydes and thia-ketones which can be prepared as described above can be converted to derivatives containing other functional groups which are normally derivable therefrom. Thus, in some of the embodiments of the invention, a thia-aldehyde or thia-ketone is converted to a derivative through contemporaneous conversion of the thia-aldehyde or thia-ketone groups to other terminal groups by chemical reactants and/or reagents. In such reactions, the thia group ($S_2$) and the $R_{10}$-$R_{13}$ groups are inert and remain unchanged in the compound. For example, the thia-bisaldehydes can be converted to hydroxy-acid derivatives wherein one of the aldehyde groups ($G^1$) is converted to a COOH group, and the other aldehyde groups ($G^2$) is converted to a $CH_2OH$ group. The hydroxy-acid derivatives are obtainable most conveniently by treating the corresponding thia-bis-aldehyde with an alkaline reagent such as an alkali metal hydroxide or alkaline earth metal hydroxide, preferably a dilute aqueous solution thereof containing from about 5 to about 50% by weight of the hydroxide in water. Such alkaline reagents may be sodium hydroxide, potassium hydroxide, lithium hydroxide, barium hydroxide, calcium hydroxide, strontium hydroxide, etc. The hydroxy-acid is isolated from the reaction mixture by acidification with a mineral acid such as hydrochloric acid. Specific examples of such hydroxy-acid derivatives include 6-hydroxy-2, 2,5,5-tetramethyl-3,4-dithiahexanoic acid; 6-hydroxy-2,2-diethyl-5-propyl-5-butyl-3,4-di-thiahexanoic acid; 6-hydroxy-2,2,5,5-tetra-ethyl-3, 4-dithiahexanoic acid; etc.

By virtue of the presence of the hydroxy group and the carboxylic group in the hydroxy-acids described above, various other sulfur-containing compounds useful in the present invention can be obtained by the conversion of such hydroxy group and/or the carboxylic group to other polar groups normally derivable therefrom. Examples of such derivatives include esters formed by esterification of either or both of the hydroxy group and the carboxylic group; amides, imides, and acyl halides formed through the carboxylic group; and lactones formed through intramolecular cyclization of the hydroxy-acid accompanied with the elimination of water. The procedures for preparing such derivatives are well known to those skilled in the art, and it is not believed necessary to unduly lengthen the specification by including a detailed description of such procedures. More specifically, the carboxylic group (COOH) can be converted to ester groups (COOR) and amide groups ($CON(R)_2$) wherein the R groups may be hydrogen or hydrocarbyl groups containing from 1 to 30 carbon atoms and more generally from 1 to about 10 carbon atcms. Specific examples of such R groups include ethyl, propyl, butyl, phenyl, etc.

The sulfur compounds characterized by structural Formula (A) wherein $G^1$ and/or $G^2$ are $R_{14}C=NR_{15}$ from the corresponding thia-aldehydes and thia-ketones. These mono- and di-imine compounds are prepared by reacting one mole of the dialdehyde or diketone with one and two moles of an amine, respectively. The amines may be monoamines or polyamines. When polyamines are reacted with the thia-aldehydes or thia-ketones, cyclic di-imines can be formed. For example, when both $G^1$ and $G^2$ in Formula (A) are $R_{14}C=NR_{15}$, the two $R_{15}$ groups together may be a hydrocarbylene group linking the two nitrogen atoms.

The amines which are useful in preparing the imine derivatives of the present invention are primary hydrocarbyl amines containing from about 2 to about 30 carbon atoms in the hydrocarbyl group, and more preferably from about 4 to about 20 carbon atoms in the hydrocarbyl group. The hydrocarbyl group may be saturated or unsaturated. Representative examples of primary saturated amines are the lower alkyl amines such as methyl amine, ethyl amine, n-propyl amine, n-butyl amine, n-amyl amine, n-hexyl amine; those known as aliphatic primary fatty amines and commercially known as "Armeen" primary amines (products available from Armak Chemicals, Chicago, Illinois). Typical fatty amines include alkyl amines such as n-hexylamine, n-octylamine, n-decylamine, n-dodecylamine, n-tetradecylamine, n-pentadecylamine, n-hexadecylamine, n-octadecylamine (stearyl amine), etc. Also suitable are mixed fatty amines such as Armak's Armeen-C, Armeen-O, Armeen-OL, Armeen-T, Armeen-HT, Armeen S and Armeen SD.

Sulfur compounds characterized by structural Formula (A) wherein $G^1$ and $G^2$ may be COOR, C≡N and $NO_2$ can be prepared by the reaction of compounds characterized by the structural formula:

wherein $R_{10}$ and $R_{11}$ are as defined above, and G is COOR, C≡N or $NO_2$, or mixtures of different compounds represented by Formula (B) with a sulfur halide or a mixture of sulfur halides and sulfur. Generally, about one mole of sulfur halide is reacted with about two moles of the compounds represented by Formula (B). In one embodiment, $R_{10}$ also may be G. In such instances, the sulfur compounds which are formed as a result of the reaction with the sulfur halide will contain four G groups which may be the same or different depending upon the starting material. For example, when a di-ketone such as 2,4-pentanedione is reacted with sulfur monochloride, the resulting product contains four ketone groups; when the starting material contains a ketone group and an ester group (e.g., ethylacetoacetate), the resulting product contains two ketone groups and two ester groups; and when the starting material contains two ester groups (e.g., diethylmalonate), the product contains four ester groups. Other combinations of functional groups can be introduced into the sulfur products utilized in the present invention and represented by Formula (A) by selecting various starting materials containing the desired functional groups.

Sulfur compounds represented by Formula (A) where $G^1$ and/or $G^2$ are C≡N groups can be prepared by the reaction of compounds represented by Formula (B) wherein G is C≡N and $R_{10}$ and $R_{11}$ are hydrogen or hydrocarbyl groups. Preferably, R is hydrogen and $R_{11}$ is a hydrocarbyl group. Examples of useful starting materials include, for example, propionitrile, butyronitrile, etc.

Compounds of Formula (A) where $G^1$ and $G^2$ are $NO_2$ groups can be prepared by (1) reacting a nitro hydrocarbon $R_{10}R_{11}C(H)NO_2$ with an alkali metal or alkaline earth metal alkoxide to form the salt of the nitro hydrocarbon, and (2) reacting said salt with sulfur monochloride in an inert, anhydrous nonhydroxylic medium to form a bis (1-nitrohydrocarbyl) disulfide. Preferably the nitro hydrocarbon is a primary nitro hydrocarbon is hydrogen and $R_{11}$ is hydrocarbyl).

The medium in which the salt is reacted with $S_2Cl_2$ must be inert to both the reactants. It is also essential that the medium be anhydrous and nonhydroxylic for the successful formation of the novel bis(1-nitrohydrocarbyl) disulfides. Examples of suitable media are ether, hexane, benzene, dioxane, higher alkyl ethers, etc.

Ordinarily, it is preferable to maintain a temperature of about 0°–10° C. during the preparation of the metal salt. However, temperatures from about 0° to 25° C. may be used in this step of the process. In the preparation of the bisdisulfide temperatures in the range of −5° to +15° C. may be used. Preferably, temperatures between about 0° to 5° C. are used in this step of the process.

The preparation of various thia-bisnitro compounds useful in the present invention is described in some detail in U.S. Pat. No. 3,479,413, and the disclosure of this patent is hereby incorporated by reference for its description.

The following Examples 10 to 13 illustrate the preparation of the sulfur compositions represented by Formula (A). Unless otherwise indicated in the examples and elsewhere in this specification and claims, all parts and of the preparation of various thia-bisnitro compounds. percentages are by weight, and all temperatures are in degrees centigrade.

EXAMPLE 10

Charge sulfur monochloride (1620 parts, 12 moles) to a 5-liter flask and warm under nitrogen to a temperature of about 53° C. whereupon add 1766 parts (24.5 moles) of isobutyraldehyde are added dropwise under nitrogen at a temperature of about 53°–60° C. over a period of about 6.5 hours. After the addition of the isobutyraldehyde is completed, heat the mixture slowly over a period of 6 hours to a temperature of about 100° C. while blowing with nitrogen. Maintain the mixture temperature at 100° C. with nitrogen blowing for a period of about 6 hours and remove volatile materials from the reaction vessel. Filter the reaction product through a filter aid. The desired product (filtrate) should contain 31.4% sulfur (theory, 31.08%). The desired reaction product, predominantly 2,2′-dithiadiisobutyraldehyde, should be recovered in about 95% yield.

EXAMPLE 11

Charge sulfur monochloride (270 parts, 2 moles) and sulfur (96 parts, 3 moles) are charged to a 1-liter flask and heat to 125° C. After maintaining the mixture at this temperature for several hours, cool the mixture to 50° C., and add 288.4 parts (4 moles) of isobutyraldehyde while blowing with nitrogen. Maintain the reaction temperature at about 55° C., and complete the addition of the isobutyraldehyde in about 4 hours. Heat the mixture to 100° C. while blowing with nitrogen and maintain at this temperature for several hours. Filter the mixture and the filtrate should contain 40.7% sulfur indicating the product to be a mixture of di-, tri- and possibly tetra-sulfide product.

EXAMPLE 12

Prepare a mixture of 412 parts (2 moles) of a dithiabisaldehyde prepared as in Example A-1 and 150 parts of toluene. Heat to 80° C. whereupon add 382 parts (2 moles) of Primere 81R dropwise while blowing with nitrogen at a temperature of 80°–90° C. Remove a water azeotrope during the addition of the Primene 81R, and after the addition is completed, raise the temperature to 110° C. while removing additional azeotrope. Strip the residue to 105° C. at reduced pressure and filter at room temperature through a filter aid. The filtrate should contain 16.9% sulfur (theory, 16.88%) and 3.64% nitrogen (theory, 3.69%).

EXAMPLE 13

Repeat the general procedure of Example A-17 except that only 206 parts of the thia-bisaldehyde of Example A-1 is utilized in the reaction.

The substantially hydrocarbon polysulfides, include principally aliphatic, cycloaliphatic, and aromatic disulfides, trisulfides, tetrasulfides, pentasulfide, or higher polysulfides. The term "polysulfide" as used herein designates compounds in which two substantially hydrocarbon radicals are joined to a group consisting of at least 2 sulfur atoms. Preferably the group consists of from 2 to 8 sulfur atoms, more preferably 2 to 6 sulfur atoms, and most preferably 2 to 4 sulfur atoms. Such polysulfides are represented, for the most part, by any of the structural formulas below:

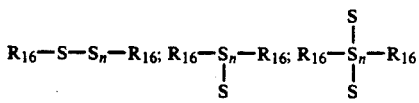

wherein $R_{16}$ is a substantially hydrocarbon radical and n is an integer preferably less than 6. The nature of the linkage between the sulfur atoms is not clearly understood, although it is believed that such linkage may be described by a single covalent bond, a double bond, or a coordinate covalent bond. The hydrocarbon polysulfides of the present invention are actually a statistical mixture of molecules which may be represented by the previous formulae. The statistical mixture may be composed of one or more species as represented by these formulae.

Polysulfides preferred for use herein are alkyl polysulfides, cycloalkyl polysulfides, aralkyl polysulfides, aryl polysulfides, alkaryl polysulfides or polysulfides having a mixture of such hydrocarbon radicals. The hydrocarbon polysufides of the present invention have from about 3 to about 24 carbon atoms in the hydrocarbon portion of the molecule. (Preferably about 3 to about 12 carbon atoms and most preferably 3 to 8 carbon atoms). By "alkyl portion of the molecule", it is meant the substantially hydrocarbon radical is shown in the formulae above. The polysulfides containing at least about 6 carbon atoms per molecule have greater oil solubility and are generally preferred. Alkyl polysulfides are preferred. Representative examples of such polysuflides are: diisobutyl trisulfide, diisopentyl trisulfide, di-n-butyl tetrasulfide, and dipentyl trisulfide. The preparation of the polysulfides may be accomplished by any of the various processes which are known and disclosed in the art including, for example, the reaction of a chlorohydrocarbon with an alkali metal polysulfide, the reaction of a mercaptan or a thiophenol with sulfur and/or sulfur halide, the reaction of saturated and unsaturated hydrocarbons with sulfur and/or sulfur halide, the reaction of a hydrocarbon monosulfide with sulfur, etc.

A discussion of the substantially hydrocarbon polysulfide occurrs in U.S. Pat. No. 3,267,033 which is hereby incorporated by reference for its disclosure of the polysufide and the processes for making them.

The sulfurized olefinic hydrocarbons are at least one sulfurization product of an aliphatic, aryliaphatic or alicyclic olefinic hydrocarbon containing from about 3 to about 30 carbon atoms.

The olefinic hydrocarbons contain at least one olefinic double bond, which is defined as a nonaromatic double bond. In its broadest sense, the olefinic hydrocarbon may be defined by the formula $R_{17}R_{18}=CR_{19}R_{20}$, wherein each of $R_{17}$, $R_{18}$, $R_{19}$ and $R_{20}$ is hydrogen or a hydrocarbon (especially alkyl or alkenyl) radical. Any two of $R_{17}$, $R_{18}$, $R_{19}$ and $R_{20}$ may also together form an alkylene or substituted alkylene group.

Monoolefinic and diolefinic compounds, particularly the former, are preferred and especially terminal monoolefinic hydrocarbons; that is, those compounds in which $R_{19}$ and $R_{20}$ are hydrogen and $R_{17}$ and $R_{18}$ are alkyl (that is, the olefin is aliphatic). Olefinic compounds having about 3-30 and especially about 3-20 carbon atoms are particularly desirable.

Propylene, isobutene and their dimers, trimers and tetramers, and mixtures thereof are especially preferred olefinic compounds. Of these compounds, isobutene and diisobutene are particuarly desirable. The sulfurizing reagent used may be, for example sulfur, a sulfur halide such as sulfur monochloride or sulfur dichloride, a mixture of hydrogen sulfide and sulfur or sulfur dioxide, or the like. Sulfur-hydrogen sulfide mixtures are often preferred and are frequently referred to hereinafter; however, it will be understood that other sulfurization agents may, when appropriate, by substituted therefor.

The amounts of sulfur and hydrogen sulfide per mole of olefinic compound are, respectively, usually about 0.1-1.5 moles. The preferred ranges are about 0.4-1.25 moles respectively, and the most desirable ranges are about 0.4-0.8 mole respectively.

The temperature range in which the sulfurization reaction is carried out is generally about 50°-350° C. The preferred range is about 100°-200° C., with about 125°-180° C., being especially suitable. The reaction is often preferably conducted under superatmospheric pressure; this may be and usually is autogenous pressure (i.e., the pressure which naturally develops during the course of the reaction) but may also be externally applied pressure. The exact pressure may vary during the course of the reaction.

It is frequently advantageous to incorporate materials useful as sulfurization catalysts in the reaction mixture. These materials may be acidic, basic or neutral, but are preferably basic materials, especially nitrogen bases including ammonia and amines, most often alkylamines. The amount of catalyst used is generally about 0.05-2.0% of the weight of the olefinic compound.

Following the preparation of the sulfurized mixture, it is preferred to remove substantially all low boiling materials, typically by venting the reaction vessel or by distillation at atmospheric pressure, vacuum distillation or stripping, or passage or an inert gas such as nitrogen through the mixture at a suitable temperature and pressure.

A further optional step in the preparation of sulfurized olefinic hydrocarbons is the treatment of the sulfurized product, obtained as described hereinabove, to reduce active sulfur. An illustrative method is treatment with an alkali metal sulfide. Other optional treatments may be employed to remove insoluble byproducts and improve such qualities as the odor, color, and staining characteristics of the sulfurized compositions. reference herein for its disclosure of suitable sulfurized olefinic hydrocarbons and procedures to prepare them. Several specific sulfurized compositions are described in the working examples thereof. The following examples illustrate the preparation of two such compositions.

EXAMPLE 14

Charge sulfur (629 parts, 19.6 moles) to a jacketed high pressure reactor fitted with an agitator and internal cooling oils. Circulate refrigerated brine through the coils to cool the reactor prior to the introduction of the gaseous reactants. After sealing the reactor, evacuating to about 6 torr and cooling, charge parts (19.6 moles) of isobutene, 334 parts (9.8 moles) of hydrogen sulfide and 7 parts of n-butylamine are charged to the reactor. Heat the reactor, using steam in the external jacket, to a temperature of about 171° C. over about 1.5 hours. A maximum pressure of 720 psig. may be reached at about 138° C. during this heat-up. Prior to reaching the peak reaction temperature, the pressure should start to decrease and continue to decrease steadily as the gaseous reactants are consumed. After about 4.75 hours at 171° C., the unreacted hydrogen sulfide and isobutene to a recovery system. After the pressure in the reactor has decreased to atmospheric, recover the sulfurized product as a liquid.

EXAMPLE 15

Following substantially the procedure of Example 14, React 773 parts of diisobutene with 428.6 parts of sulfur and 143.6 parts of hydrogen sulfide in the presence of 2.6 parts of n-butylamine, under autogenous pressure at a temperature of about 150°–155° C. Remove volatile materials and recover the sulfurized product as a liquid.

A further discussion of the sulfurized olefinic hydrocarbons occurrs in U.S. Pat. No. 4,560,488, which is hereby incorporated by reference for its disclosure of the sulfurized olefins and procedures for making them.

The sulfur containing compounds of the present invention are present in quantities ranging from about 1% to about 15% by weight. Preferably, the sulfur containing compounds are present in the range of about 2% to about 10%, with 2.5% to 8% being the most preferred range.

In concentrate compositions, the sulfur containing compounds are present in the range of 0.01 to 90% by weight, with 25% to 90% by weight preferred and 50% to 90% by weight most preferred.

The sulfur containing compound may be present in any amount effective to improve the antiwear and extreme pressure properties of lubricating compositions containing the phosphorus acids and salts of the present invention.

Lubricating composition may be prepared by adding from about 0.05 to about 10% by weight of the compositions of Examples 1–4 and from about 1% to about 15% by weight of the compositions of Examples 5–10 to an oil.

Concentrate compositions may be prepared by adding from 0.05 to 90% of the compositions of Examples 1–4 and from 0.05 to 90% of the composition of Examples 5–10 to an oil.

What is claimed is:

1. A phosphorus containing lubricating composition, comprising: an oil of lubricating viscosity and (A) a salt prepared from a hydroxyalkane phosphonic acid of the formula:

$$R-X-\left(\begin{matrix} H \\ | \\ C \\ | \\ H \end{matrix}\right)_n \begin{matrix} OH & O \\ | & \| \\ C-P-OH \\ | & | \\ Y & OH \end{matrix}$$

wherein X is oxygen, sulfur, or a secondary amino group, n is an integer from 1 to 8, Y is hydrogen, alkyl or a phosphonic acid group and R is an alkyl group having from about 6 to about 24 carbon atoms, and (B) a base.

2. The composition as claimed in claim 1, wherein X is sulfur or oxygen.

3. The composition as claimed in claim 1v, wherein the base comprises
   (A) a detergent,
   (B) a dispersant, or
   (C) an amine.

4. The composition as claimed in claim 3, wherein the amine is represented by the formula:

$$R_1-N-R_3 \\ | \\ R_2$$

wherein $R_1$, $R_2$ and $R_3$ are each independently hydrogen or hydrocarbyl.

5. The composition as claimed in claim 4, wherein $R_2$ and $R_3$ are hydrogens and $R_1$ is alkyl having from 6 to 30 carbon atoms.

6. The composition as claimed in claim 4, wherein $R_1$ and $R_2$ are alkyl having 6 to 30 carbon atoms.

7. The composition as claimed in claim 4, wherein $R_1$ is alkenyl having from 6 to 30 carbon atoms and $R_2$ and $R_3$ are each independently hydrogen or hydrocarbyl.

8. The composition as claimed in claim 4, wherein $R_1$ is a sulfurized alkenyl having from 6 to 30 carbon atoms.

9. The composition as claimed in claim 4, wherein at least one of $R_1$, $R_2$ and $R_3$ is an alkylhydroxy or alkoxy group.

10. The composition as claimed in claim 9, wherein the alkylhydroxy or alkoxy group has an alkyl portion containing from 1 to about 30 carbon atoms.

11. The composition as claimed in claim 3, wherein the dispersant comprises:
    (a) a Mannich dispersant;
    (b) a succinimide dispersant;
    (c) a nitrogen containing ester type dispersant; or
    (d) a dispersant viscosity improver.

12. The composition as claimed in claim 11, wherein the succinimide dispersant is the reaction product of an alkenyl carboxylic acid acylating agent having from 30 to 500 carbon atoms with a polyalkylene polyamine.

13. The composition as claimed in claim 7, wherein the succinimide dispersant is the reaction product of a polyisobutylene succinic anhydride having an number average molecular weight between 800 and 2000 with a polyalkylene polyamine.

14. The composition as claimed in claim 3, wherein the detergent is a neutral or basic metal salt.

15. The composition as claimed in claim 14, wherein the neutral or basic metal salt is an alkali, alkaline earth or transition metal salt of an aliphatic or aromatic acid.

16. A lubricating composition comprising an oil of lubricating viscosity and an amount effective to improve the antiwear and extreme pressure properties of a salt prepared from a hydroxyalkane phosphonic acid of the formula:

$$R-X-\left(\begin{matrix} H \\ | \\ C \\ | \\ H \end{matrix}\right)_n \begin{matrix} OH & O \\ | & \| \\ C-P-OH \\ | & | \\ Y & OH \end{matrix}$$

wherein X is oxygen, sulfur or a secondary amino grup, n is an integer from 1 to 8, Y is hydrogen, alkyl or a phosphonic acid group and R is an alkyl group having from 1 to about 100 carbon atoms, and a base.

17. The lubricating composition as claimed in claim 16, wherein R is an alkyl group containing 1 to about 30 carbon atoms.

18. The lubricating composition as claimed in claim 16, wherein X is sulfur or oxygen.

19. The lubricating composition as claimed in claim 17, wherein the base comprises
(A) a detergent;
(B) a dispersant; or
(C) an amine represented by the formula:

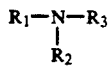

wherein $R_1$, $R_2$ and $R_3$ are each independently hydrogen or hydrocarbyl.

20. The lubricating composition as claimed in claim 19, wherein $R_2$ and $R_3$ are hydrogen and $R_1$ is alkyl having from 6 to 30 carbon atoms.

21. The lubricating composition as claimed in claim 19, wherein the dispersant comprises
(a) a Mannich dispersant;
(b) a succinimide dispersant;
(c) a nitrogen containing ester type dispersant; or
(d) a dispersant viscosity improver.

22. The lubricating composition as claimed in claim 21, wherein the succinimide dispersant is the reaction product of an alkenyl carboxylic acid acylating agent having from 30 to 500 carbon atoms with a polyalkylene polyamine.

23. The lubricating composition as claimed in claim 22, wherein the succinimide dispersant is the reaction product of a polyisobutylene succinic anhydride having an number average molecular weight between 800 and 2000 with a polyalkylene polyamine.

24. The lubricating composition as claimed in claim 19, wherein the detergent is an overbased or neutral composition of an alkali, alkaline earth metal or transition metal salt of an aliphatic or aromatic acid.

25. The lubricating composition as claimed in claim 16, further comprising:
an amount effective to improve the antiwear and extreme pressure properties of a sulfur containing compound of the structural formula (A):

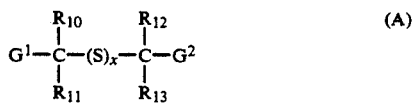

$R_{10}$, $R_{11}$, $R_{12}$ and $R_{13}$ are independently H or hydrocarbyl groups, or at least one of
$R_{10}$ and $R_{12}$ is $G^1$ or $G^2$, or at least one combination of $R_{10}$ and $R_{11}$ or $R_{12}$ and $R_{13}$ together forms alkylene groups containing about 4 to about 7 carbon atoms;
$G^1$ and $G^2$ are each independently C(X)R, COOR, C=N, $R_{14}C=NR_{15}$,CON(R)$_2$ or NO$_2$, and $G^1$ also may be CH$_2$OH, wherein X is O or S, R and each R are independently H or a hydrocarbyl group, R is H or a hydrocarbyl group; or
when both $G^1$ and $G^2$ are $R_{14}C=NR_{15}$, the two $R_{15}$ groups together may be a hydrocarbylene group linking the two nitrogen atoms; or
when $G^1$ is CH$_2$OH and $G^2$ is COOR, a lactone may be formed by intramolecular condensation of $G^1$ and $G^2$; and
x is an integer from 1 to about 8.

26. The composition of claim 25 wherein x is an integer from 1 to about 4.

27. The composition of claim 25 wherein $G^1$ and $G^2$ are identical.

28. The composition of claim 25 wherein $R_{10}$ and $R_{12}$ H or hydrocarbyl groups and $G^1$ and $G^2$ are C(O)H.

29. The composition of claim 25, wherein $R_{10}$, $R_{11}$, $R_{12}$ and $R_{13}$ are hydrogen or hydrocarbyl groups, and both $G^1$ and $G^2$ are NO$_2$ groups.

30. The composition of claim 25 wherein $G^1$ and $G^2$ are C(X)R wherein R is a hydrocarbyl group.

31. The composition of claim 25 wherein $R_{10}$, $R_{11}$, $R_{12}$ and $R_{13}$ are each independently hydrogen or hydrocarbyl groups and $G^1$ and $G^2$ are $R_{14}$—C=NR$_{15}$ groups wherein $R_{14}$ and $R_{15}$ are each independently hydrogen, hydrocarbyl groups or the two $R_{15}$ groups together form a hydrocarbylene group joining the two nitrogen atoms.

32. The composition of claim 25 wherein $R_{11}$ and $R_{13}$ are hydrogen or hydrocarbyl groups and $R_{10}$, $R_{12}$, $G^1$ and $G^2$ are C(O)R wherein R is a hydrocarbyl group.

33. The composition of claim 25 wherein $R_{11}$ and $R_{13}$ are hydrogen or hydrocarbyl groups, $R_{10}$ and $R_{12}$ are COOR groups, and $G^1$ and $G^2$ are C(O)R groups wherein each R is hydrogen or a hydrocarbyl group.

34. The composition of claim 32 wherein each $R_{11}$ and $R_{13}$ are hydrocarbyl groups.

35. The composition of claim 25 wherein $R_{11}$ and $R_{13}$ are hydrogen or hydrocarbyl groups, and $R_{10}$, $R_{12}$, $G^1$ and $G^2$ each independently COOR groups wherein each R is a hydrocarbyl group.

36. The composition of claim 25 wherein $R_{10}$ and $R_{12}$ are each independently hydrogen or hydrocarbyl groups, $G^1$ is CH$_2$OH, and $G^2$ is COOR wherein R is a hydrocarbyl group.

37. The composition of claim 25 wherein $R_{10}$, $R_{11}$, $R_{12}$ and $R_{13}$ are H or lower hydrocarbyl groups containing from 1 to about 7 carbon atoms.

38. The lubricating composition as claimed in claim 16, further comprising an antiwear and extreme pressure improving amount of a hydrocarbon polysulfide.

39. The lubricating composition as claimed in claim 16, further comprising an antiwear and extreme pressure improving amount of a sulfurized olefinic hydrocarbon.

40. The composition of claim 30, wherein the hydrocarbon polysulfide has from about 3 to about 24 carbon atoms in the alkyl portion of the molecule and having a group consisting of at least 2 sulfur atoms.

41. The composition as claimed in claim 38 wherein the hydrocarbon polysulfide is an alkyl polysulfide having from about 3 to about 24 carbon atoms in the alkyl portion of the molecule.

42. The composition as claimed in claim 39 wherein the sulfurized olefinic hydrocarbon is prepared by reacting an olefinic hydrocarbon with a sulfurizing agent at about 50° to about 350° in the ratio of about 0.1 to 1.3 moles of sulfurizing agent to one mole of olefinic hydrocarbon.

43. The composition claimed in claim 39 wherein the olefinic hydrocarbon is an aliphatic olefin having from about 3 to about 30 carbon atoms.

44. A grease composition comprising the composition of claim 1 and a thickening agent.

45. The composition of claim 1 comprising from about 0.05 to 90% by weight of the hydroxyalkane phosphonic acid salt.

* * * * *